(12) United States Patent
Watanabe et al.

(10) Patent No.: US 9,522,979 B2
(45) Date of Patent: Dec. 20, 2016

(54) FLUORINE-CONTAINING SILICON COMPOUND, METHOD FOR PRODUCING SAME, AND METHOD FOR PRODUCING FLUORINE-CONTAINING SILICON RESIN

(71) Applicant: SHIN-ETSU CHEMICAL CO., LTD., Tokyo (JP)

(72) Inventors: Takeru Watanabe, Jyoetsu (JP); Yoshinori Taneda, Jyoetsu (JP); Tsutomu Ogihara, Jyoetsu (JP); Seiichiro Tachibana, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/981,474

(22) Filed: Dec. 28, 2015

(65) Prior Publication Data
US 2016/0229960 A1    Aug. 11, 2016

(30) Foreign Application Priority Data

Feb. 6, 2015 (JP) ................. 2015-022211

(51) Int. Cl.
| | | |
|---|---|---|
| *C08G 77/24* | (2006.01) | |
| *C07F 7/18* | (2006.01) | |
| *C08G 79/08* | (2006.01) | |
| *C08G 77/00* | (2006.01) | |

(52) U.S. Cl.
CPC ............... *C08G 77/24* (2013.01); *C07F 7/184* (2013.01); *C07F 7/188* (2013.01); *C07F 7/1836* (2013.01); *C08G 79/08* (2013.01); *C08G 77/80* (2013.01)

(58) Field of Classification Search
CPC ........ C08G 77/24; C07F 7/1836; C07F 7/184; C07F 7/188
See application file for complete search history.

(56) References Cited

U.S. PATENT DOCUMENTS

| | | | | |
|---|---|---|---|---|
| 8,563,762 B2 * | 10/2013 | Snow | ................ | B05D 1/185 556/173 |
| 2004/0248032 A1 | 12/2004 | Zampini et al. | | |
| 2012/0052685 A1 | 3/2012 | Ogihara et al. | | |

FOREIGN PATENT DOCUMENTS

| | | |
|---|---|---|
| JP | 2004-295104 A | 10/2004 |
| JP | 2012-053253 A | 3/2012 |
| JP | 5178858 B2 | 4/2013 |

OTHER PUBLICATIONS

Yamamoto, Yohsuke, Yasuhiro Takeda, and Kin-ya Akiba. "Intramolecular cyclization of o-silylbenzyl alcohols with elimination of hydrocarbon via hypervalent silicon intermediates: Effect of structure on the selectivity for elimination." Tetrahedron Letters 30.6 (1989): 725-728.*
Cai, Yudong, and Brian P. Roberts. "Intramolecular radical-chain hydrosilylation catalysed by thiols: cyclisation of alkenyloxysilanes." Journal of the Chemical Society, Perkin Transactions 1 3 (1998): 467-476.*
Nguyen, Phuc T., Wylie S. Palmer, and K. A. Woerpel. "Stereospecific and regioselective isocyanide insertions into siliranes and reactions of the resulting iminosilacyclobutanes." The Journal of organic chemistry 64.6 (1999): 1843-1848.*
Anger, Christian A., et al. "Oxasilacycles Leading to UV-Curable Polymers: Synthesis and Application." Macromolecules 47.24 (2014): 8497-8505.*

* cited by examiner

*Primary Examiner* — Liam J Heincer
*Assistant Examiner* — Nicholas Hill
(74) *Attorney, Agent, or Firm* — Oliff PLC

(57) ABSTRACT

The present invention provides a fluorine-containing silicon compound represented by the general formula (1),

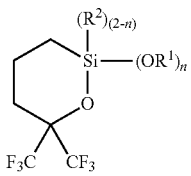

(1)

wherein each $R^1$ independently represents a hydrocarbon group having 1 to 6 carbon atoms; each $R^2$ independently represents a hydrogen atom or a hydrocarbon group having 1 to 6 carbon atoms; and n is an integer satisfying $0 \leq n \leq 2$. There can be provided a fluorine-containing silicon compound having good storage stability and useful as a raw material of a composition for forming a silicon-containing intermediate film and a silicon-containing photoresist composition used for a fine processing in the manufacturing process of a semiconductor device.

8 Claims, No Drawings

FLUORINE-CONTAINING SILICON COMPOUND, METHOD FOR PRODUCING SAME, AND METHOD FOR PRODUCING FLUORINE-CONTAINING SILICON RESIN

BACKGROUND OF THE INVENTION

Field of the Invention

The present invention relates to a novel fluorine-containing silicon compound, a method for producing the same, and a method for producing a fluorine-containing silicon resin using the same.

Description of the Related Art

The introduction of a hydrolysable fluorine-containing silicon compound is useful for adjusting various properties of a condensation resin. For example, in the multilayer resist method used for a fine processing in the manufacturing process of a semiconductor device or the like, it has been proposed to apply this compound to a composition for forming a silicon-containing film used as an intermediate layer or a silicon-containing photoresist composition (Patent Documents 1 and 2).

In Patent Document 2, 1,1,1-trifluoro-5-(triethoxysilyl)-2-(trifluoromethyl)-2-pentanol represented by the formula (6) has been proposed as the hydrolysable fluorine-containing silicon compound particularly useful. However, said compound has a critical fault in storage stability and thus is unsuitable for practical use. Accordingly, there has been demanded a fluorine-containing silicon compound served as an alternative compound and having functions equivalent to said compound as a raw material of a condensation resin.

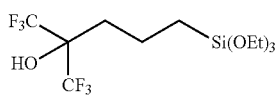
(6)

PRIOR ART DOCUMENTS

Patent Documents

Patent Document 1: Japanese Patent Laid-Open Publication No. 2012-53253

Patent Document 2: Japanese Patent No. 5178858

SUMMARY OF THE INVENTION

The present invention was accomplished in view of the above circumstances, and an object thereof is to provide a fluorine-containing silicon compound having good storage stability and useful as a raw material of a composition for forming a silicon-containing intermediate film and a silicon-containing photoresist composition used for a fine processing in the manufacturing process of a semiconductor device.

To accomplish the object, the present invention provides a fluorine-containing silicon compound represented by the general formula (1),

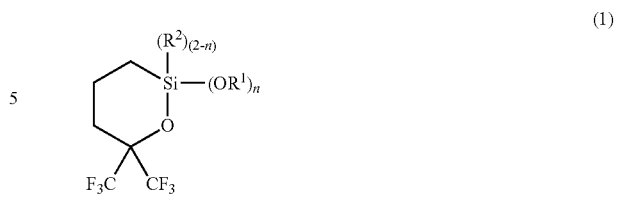
(1)

wherein each $R^1$ independently represents a hydrocarbon group having 1 to 6 carbon atoms; each $R^2$ independently represents a hydrogen atom or a hydrocarbon group having 1 to 6 carbon atoms; and n is an integer satisfying 0 n 2.

Such a fluorine-containing silicon compound has good storage stability and is useful as a raw material of a composition for forming a silicon-containing intermediate film and a silicon-containing photoresist composition used for a fine processing in the manufacturing process of a semiconductor device.

The fluorine-containing silicon compound is preferably used as a raw material of a resin contained in a composition for forming a silicon-containing intermediate film or a silicon-containing photoresist composition.

The fluorine-containing silicon compound of the present invention can be easily mass-produced, and has good storage stability. Therefore, this compound is suitable as a raw material of a resin contained in a composition for forming a silicon-containing intermediate film or a silicon-containing photoresist composition.

In addition, the present invention provides a method for producing the above-mentioned fluorine-containing silicon compound, comprising subjecting a fluorine-containing silicon compound represented by the general formula (2) to intramolecular condensation,

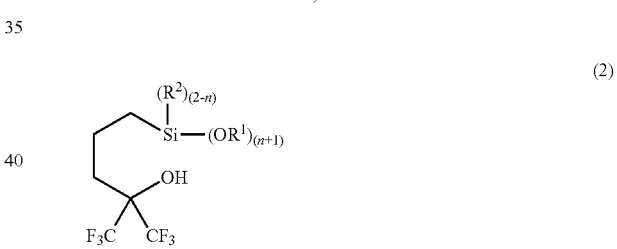
(2)

wherein $R^1$, $R^2$, and n have the same meanings as defined above.

The fluorine-containing silicon compound of the present invention can be produced by such a method, for example.

In addition, the present invention provides a method for producing the above-mentioned fluorine-containing silicon compound, comprising reacting a fluorine-containing compound represented by the formula (3) with a silicon compound represented by the general formula (4),

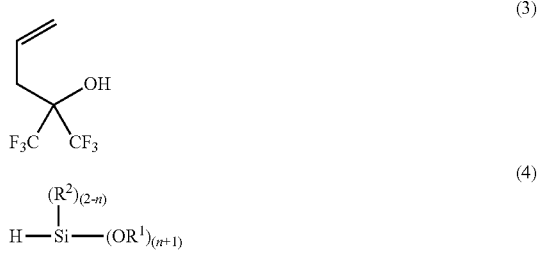
(3)

(4)

wherein R¹, R², and n have the same meanings as defined above.

The fluorine-containing silicon compound of the present invention can also be produced by such a method.

Furthermore, the present invention provides a method for producing a fluorine-containing silicon resin, comprising hydrolysis condensation of one or more compounds selected from the group consisting of a hydrolysable silicon compound represented by the general formula (5-1) and a reactive compound represented by the general formula (5-2) with one or more fluorine-containing silicon compounds mentioned above,

(5-1)

(5-2)

wherein each $R^3$ independently represents a hydrogen atom or a monovalent organic group having 1 to 30 carbon atoms; each $R^4$ independently represents a hydrocarbon group having 1 to 6 carbon atoms; m1 is an integer satisfying $0 \leq m1 \leq 3$; $R^5$ and $R^6$ independently represent a hydrogen atom or a monovalent organic group having 1 to 30 carbon atoms; U represents any element belonging to the group of III, IV, or V in the periodic table, except for carbon and silicon; m2+m3+m4 is a number of valency determined by U; and each of m2, m3, and m4 is an integer of 0 or more.

When such a producing method is employed, a fluorine-containing silicon resin can be easily produced by using the fluorine-containing silicon compound of the present invention in the same manner as the conventional method.

The fluorine-containing silicon compound of the present invention can be easily mass-produced, has good storage stability, and is useful as a raw material of a composition for forming a silicon-containing intermediate film and a silicon-containing photoresist composition used for a fine processing in the manufacturing process of a semiconductor device. Therefore, its industrial application value is extremely high. In addition, the fluorine-containing silicon compound of the present invention can be produced by an appropriate method according to the structure of the compound.

Further, when the inventive method for producing a fluorine-containing silicon resin is employed, a fluorine-containing silicon resin can be easily produced by using the fluorine-containing silicon compound of the present invention in the same manner as the conventional method.

DETAILED DESCRIPTION OF THE PREFERRED EMBODIMENTS

As mentioned above, there has been demanded a fluorine-containing silicon compound having good storage stability and useful as a raw material of a composition for forming a silicon-containing intermediate film and a silicon-containing photoresist composition used for a fine processing in the manufacturing process of a semiconductor device.

The present inventors have earnestly investigated a hydrolysable fluorine-containing silicon compound having good storage stability as well as functions equivalent to the aforementioned 1,1,1-trifluoro-5-(triethoxysilyl)-2-(trifluoromethyl)-2-pentanol. As a result, they found the fluorine-containing silicon compound represented by the general formula (1), and further developed an industrial method for producing the same, thereby bringing the present invention to completion.

That is, the present invention provides a fluorine-containing silicon compound represented by the general formula (1),

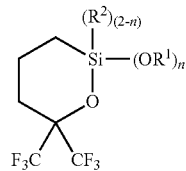
(1)

wherein each $R^1$ independently represents a hydrocarbon group having 1 to 6 carbon atoms; each $R^2$ independently represents a hydrogen atom or a hydrocarbon group having 1 to 6 carbon atoms; and n is an integer satisfying $0 \leq n \leq 2$.

Hereinafter, the present invention will be described in detail, but the present invention is not limited thereto.

Herein, Me, Et, Pr, $^i$Pr, and Ph denote a methyl group, an ethyl group, a propyl group, an isopropyl group, and a phenyl group, respectively.

[Fluorine-Containing Silicon Compound]

The fluorine-containing silicon compound of the present invention is represented by the general formula (1),

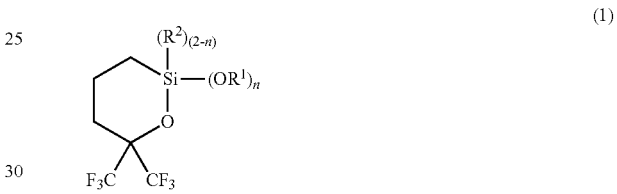
(1)

wherein each $R^1$ independently represents a hydrocarbon group having 1 to 6 carbon atoms; each $R^2$ independently represents a hydrogen atom or a hydrocarbon group having 1 to 6 carbon atoms; and n is an integer satisfying 0 n 2.

In the general formula (1), $R^1$ independently represents a hydrocarbon group having 1 to 6 carbon atoms, and $R^2$ independently represents a hydrogen atom or a hydrocarbon group having 1 to 6 carbon atoms. Illustrative examples of $R^1$ include a methyl group, an ethyl group, a propyl group, an isopropyl group, a butyl group, an isobutyl group, a s-butyl group, a t-butyl group, a pentyl group, a neopentyl group, a cyclopentyl group, a hexyl group, a cyclohexyl group, and a phenyl group, and illustrative examples of $R^2$ include a hydrogen atom, a methyl group, an ethyl group, a propyl group, an isopropyl group, a butyl group, an isobutyl group, a s-butyl group, a t-butyl group, a pentyl group, a neopentyl group, a cyclopentyl group, a hexyl group, a cyclohexyl group, and a phenyl group, but there are not limited thereto. As $R^1$, a methyl group, an ethyl group, a propyl group, and an isopropyl group are particularly preferable. As $R^2$, a methyl group, an ethyl group, and a phenyl group are particularly preferable. "n" is an integer satisfying $0 \leq n \leq 2$, particularly preferably 1 or 2.

Specifically, the compounds shown by the following formulae are preferable as the fluorine-containing silicon compound of the present invention, but it is not limited thereto.

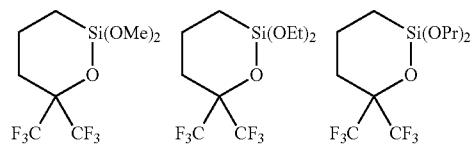

-continued

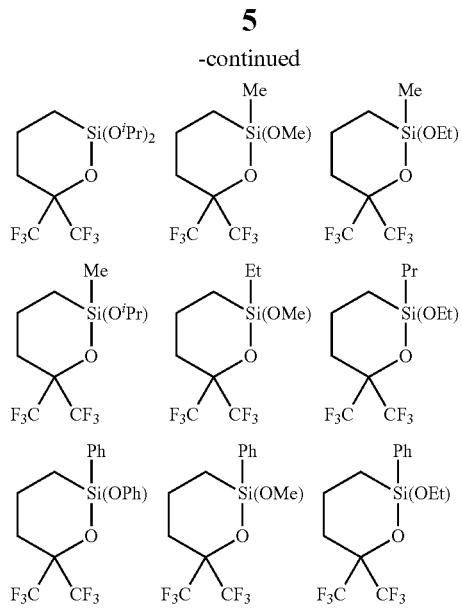

In general, the aforementioned conventional fluorine-containing silicon compound, 1,1,1-trifluoro-5-(triethoxysilyl)-2-(trifluoromethyl)-2-pentanol (6), which is poor in storage stability, is practically used after hydrolysis condensation into a resin. In the hydrolysis condensation reaction, an immediate product (7) is produced by hydrolysis at first, and then a product (8) is provided by condensation, as shown in the following chemical equation.

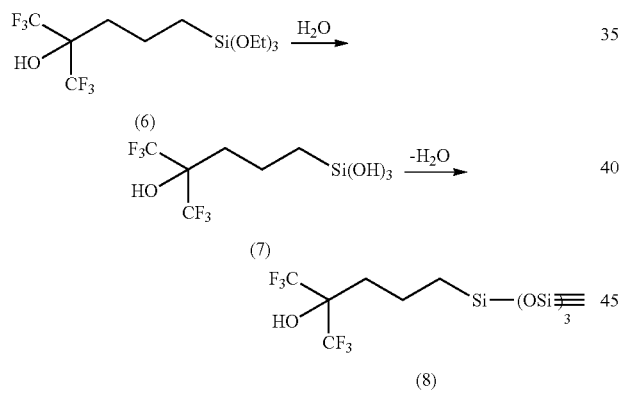

On the other hand, the fluorine-containing silicon compound (1) of the present invention also can be formed into a resin by hydrolysis condensation. In this reaction, an immediate product (7') is produced by hydrolysis at first, and then a product (8') is provided by condensation, as shown in the following chemical equation.

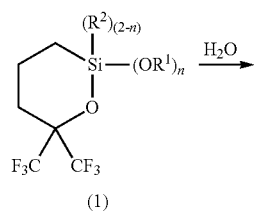

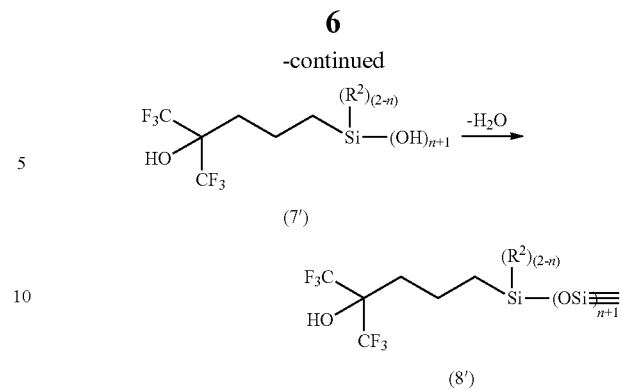

wherein $R^1$, $R^2$, and n have the same meanings as defined above.

As mentioned above, the fluorine-containing silicon compound (1) of the present invention is a novel compound different from the conventional 1,1,1-trifluoro-5-(triethoxysilyl)-2-(trifluoromethyl)-2-pentanol (6), and has more excellent storage stability compared with the conventional one, although after resinification through the hydrolysis condensation, it has similar structure and equivalent performance to the resin produced from the conventional 1,1,1-trifluoro-5-(triethoxysilyl)-2-(trifluoromethyl)-2-pentanol (6).

[Method for Producing a Fluorine-Containing Silicon Compound]

The fluorine-containing silicon compound of the present invention can be produced by selecting an appropriate method according to the structure of the compound. Illustrative examples thereof include: (a) a producing method by intramolecular condensation of a fluorine-containing silicon compound having an alcoholic hydroxyl group (hereinafter, referred to as method (a)); and (b) a producing method by reaction of 1,1,1-trifluoro-2-(trifluoromethyl)-4-penten-2-ol with an alkoxyhydrosilane compound (hereinafter, referred to as method (b)), but it is not limited to these methods. In the following, a detailed explanation is given.

In method (a), specifically, a fluorine-containing silicon compound represented by the general formula (2) is subjected to intramolecular condensation,

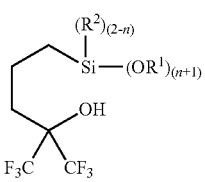

wherein $R^1$, $R^2$, and n have the same meanings as defined above.

As shown in the following chemical equation, the fluorine-containing silicon compound of the present invention can be obtained by subjecting the fluorine-containing silicon compound represented by the general formula (2) to intramolecular condensation,

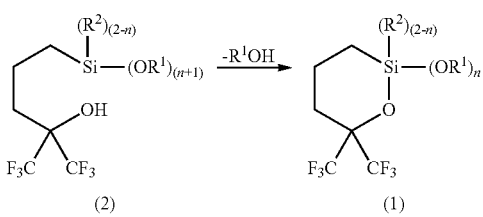

wherein $R^1$, $R^2$, and n have the same meanings as defined above.

The fluorine-containing silicon compound (2) used as the raw material can be obtained, for example, by the producing method described in Japanese Patent Laid-Open Publication No. 2004-295104. The intramolecular condensation reaction proceeds by heating or reducing pressure of the fluorine-containing silicon compound (2) in the presence of a catalyst or without a catalyst, in a solvent or without a solvent.

In the intramolecular condensation reaction, an acid catalyst or a basic catalyst may be added to accelerate the reaction speed. Examples of the acid catalyst include inorganic acids such as sulfuric acid, hydrochloric acid, phosphoric acid, and perchloric acid; Lewis acids such as boron trifluoride, boron trifluoride-diethyl ether complex, dibutyltin oxide, aluminum chloride, zinc chloride, titanium tetrachloride, and titanium tetramethoxide; sulfonic acids such as methanesulfonic acid and p-toluenesulfonic acid; salts such as potassium hydrogensulfate, calcium chloride, magnesium chloride, and pyridinium p-toluenesulfonate; carboxylic acids such as oxalic acid and trifluoroacetic acid; and acidic resins such as a cation-exchanged resin. A suitable catalyst may be selected from these, and used solely or as a mixture, depending on the reaction condition. The amount of the acid catalyst to be used is preferably 0 to 10 mol, particularly 0 to 5 mol per 1 mol of the fluorine-containing silicon compound (2).

Examples of the basic catalyst include amines such as pyridine, triethylamine, diisopropylethylamine, 4-dimethylaminopyridine, and imidazole; metal alkoxides such as sodium methoxide, sodium ethoxide, and potassium t-butoxide; carbonates such as sodium carbonate, potassium carbonate, and cesium carbonate; hydroxides such as sodium hydroxide, potassium hydroxide, and tetramethylammonium hydroxide; metal hydrides such as sodium hydride and potassium hydride; organometallic compounds such as butyl lithium and ethyl magnesium bromide; and metal amides such as lithium diisopropyl amide. A suitable catalyst may be selected from these, and used solely or as a mixture, depending on the reaction condition. The amount of the basic catalyst to be used is preferably 0 to 10 mol, particularly 0 to 5 mol per 1 mol of the fluorine-containing silicon compound (2).

When the reaction is performed in a solvent, example of the reaction solvent include hydrocarbon solvents such as hexane, heptane, benzene, toluene, and xylene; ether solvents such as diethyl ether, dibutyl ether, tetrahydrofuran, 1,4-dioxane, and diglyme; chlorinated solvents such as methylene chloride, chloroform, and 1,2-dichloroethylene; aprotic polar solvents such as N,N-dimethylformamide, N,N-dimethylacetamide, dimethyl sulfoxide, and N-methylpyrrolidone; ester solvents such as ethyl acetate and butyl acetate; ketone solvents such as acetone and 2-butanone; nitrile solvents such as acetonitrile. A suitable solvent may be selected from these, and used solely or as a mixture, depending on the reaction condition.

The reaction temperature is preferably determined in the range of 0° C. to reflux temperature of the solvent, depending the reaction speed. In particular, the reaction is preferably performed with a solvent having a boiling point higher than that of alcohol $R^1OH$ produced by the reaction, at a temperature higher than the boiling point of $R^1OH$ while removing the produced $R^1OH$, in view of enhancement of the reaction rate and reduction in the reaction time. When the reaction is performed under reduced pressure, the reaction pressure and temperature conditions are preferably such that alcohol $R^1OH$ evaporates, while the product, fluorine-containing silicon compound (1), does not evaporate. In particular, it is preferable to apply a proper condition in the range of 10 Pa to 100 kPa and 0 to 200° C.

In view of yield, the reaction time is desirably determined by monitoring the reaction process by gas chromatography (GC) to bring the reaction to completion. Usually the reaction time is about 0.5 to 24 hours. If the reaction mixture already has a sufficient purity, the reaction mixture can be directly used as the final product. However, if necessary, the reaction mixture may be purified by various purification methods such as distillation, filtration, washing, column separation, and solid absorbent, before use. To remove trace impurities such as catalyst and achieve high purity, purification by distillation is particularly preferable.

In method (b), specifically, a fluorine-containing compound represented by the formula (3) (1,1,1-trifluoro-2-(trifluoromethyl)-4-penten-2-ol) is reacted with a silicon compound represented by the general formula (4) (alkoxyhydrosilane compound) in the presence of a transition metal catalyst by heating,

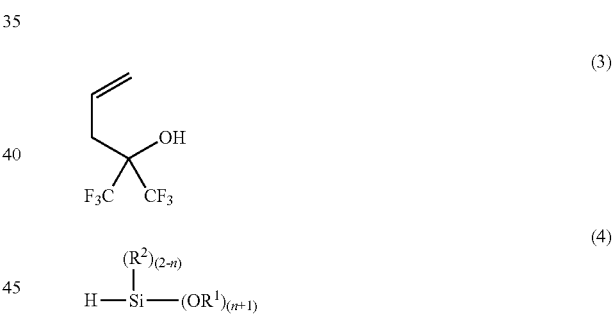

wherein $R^1$, $R^2$, and n have the same meanings as defined above.

As shown in the following chemical equation, the fluorine-containing silicon compound of the present invention can be obtained by heating the fluorine-containing compound represented by the formula (3) and the silicon compound represented by the general formula (4) in the presence of a transition metal catalyst to conduct the reaction,

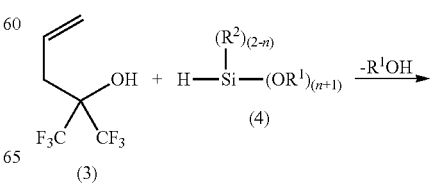

-continued

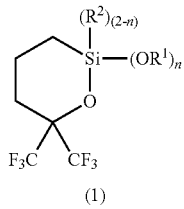

(1)

wherein $R^1$, $R^2$, and n have the same meanings as defined above.

Specifically, the silicon compound (4) used as the raw material is preferably, but not particularly limited to, trimethoxy silane, triethoxy silane, tripropoxy silane, triisopropoxy silane, methyl dimethoxy silane, methyl diethoxy silane, methyl diisopropoxy silane, ethyl dimethoxy silane, propyl diethoxy silane, phenyl diphenoxy silane, phenyl dimethoxy silane, phenyl diethoxy silane, dimethoxy silane, diethoxy silane, and diisopropoxy silane.

The formulation ratio between the fluorine-containing compound (3) and the silicon compound (4) is not particularly limited, but the silicon compound (4) is preferably in the range of 0.5 to 2 mol, in particular 0.7 to 1.3 mol per 1 mol of the fluorine-containing compound (3), in view of reactivity and productivity.

As the transition metal catalyst used in the reaction, a platinum catalyst is particularly preferable because of good reactivity and productivity. Examples of the platinum catalyst include chloroplatinic acid, alcohol solution of chloroplatinic acid, a toluene or xylene solution of platinum-1,3-divinyl-1,1,3,3-tetramethyldisiloxane complex, tetrakistriphenylphosphine platinum, dichlorobistriphenylphosphine platinum, dichlorobisacetonitrile platinum, dichlorobisbenzonitrile platinum, and dichlorocyclooctadiene platinum. The amount of the transition metal catalyst to be used is not particularly limited, but it is preferably 0.000001 to 0.01 mol, in particular 0.00001 to 0.001 mol, per 1 mol of the fluorine-containing compound (3), in view of reactivity and productivity.

In the above reaction, active hydrogen compound may be added to accelerate the reaction speed. Illustrative examples of the active hydrogen compound include amides such as acetamide and formamide, ammonium salts such as ammonium carbonate and ammonium hydrogencarbonate, carboxylic acids such as formic acid, acetic acid, and benzoic acid, but is not particularly limited.

In the reaction, a solvent may be used, although the reaction may proceed without a solvent. Examples of the usable solvent include hydrocarbon solvents such as pentane, hexane, cyclohexane, heptane, isooctane, benzene, toluene, and xylene; ether solvents such as diethyl ether, tetrahydrofuran, and dioxane; ester solvents such as ethyl acetate and butyl acetate; aprotic polar solvents such as acetonitrile and N,N-dimethylformamide; and chlorinated solvents such as dichloromethane and chloroform. These solvents may be used solely or as a mixture of two or more kinds.

The reaction temperature in the above reaction is not particularly limited, and may be increased during the reaction, if necessary. Preferable range thereof is 30 to 200° C., in particular 50 to 150° C. Similarly to method (a), the reaction is preferably performed while removing $R^1OH$ produced during the reaction, in view of enhancement of the reaction rate and reduction in the reaction time.

In view of yield, the reaction time is desirably determined by monitoring the reaction process by gas chromatography (GC) to bring the reaction to completion. Usually the reaction time is about 0.5 to 24 hours. If the reaction mixture already has a sufficient purity, the reaction mixture can be directly used as the final product. However, if necessary, the reaction mixture may be purified by various purification methods such as distillation, filtration, washing, column separation, and solid absorbent. To remove trace impurities such as catalyst and achieve high purity, purification by distillation is particularly preferable.

As mentioned above, the compound of the present invention can be easily produced, for example, by the methods (a) and (b). Such a fluorine-containing silicon compound of the present invention has good storage stability, and is suitably used as a raw material of a resin (base resin) contained in a composition for forming a silicon-containing intermediate film or a silicon-containing photoresist composition.

[Method for Producing a Fluorine-Containing Silicon Resin]

In addition, the present invention provides a method for producing a fluorine-containing silicon resin, comprising hydrolysis condensation of one or more compounds selected from the group consisting of a hydrolysable silicon compound represented by the general formula (5-1) and a reactive compound represented by the general formula (5-2) with one or more fluorine-containing silicon compounds of the present invention, as raw material monomers,

wherein each $R^3$ independently represents a hydrogen atom or a monovalent organic group having 1 to 30 carbon atoms; each $R^4$ independently represents a hydrocarbon group having 1 to 6 carbon atoms; m1 is an integer satisfying $0 \leq m1 \leq 3$; $R^5$ and $R^6$ independently represent a hydrogen atom or an organic group having 1 to 30 carbon atoms; U represents any element belonging to the group of III, IV, or V in the periodic table, except for carbon and silicon; m2+m3+m4 is a number of valency determined by U; and each of m2, m3, and m4 is an integer of 0 or more.

In particular, the above fluorine-containing silicon resin is suitably used for a composition for forming a silicon-containing intermediate film. For example, in the multilayer resist method used in a lithography for semiconductor manufacturing, when an organic film, a silicon-containing film, and a photoresist film are successively formed and then a resist pattern is formed, use of a composition for forming a silicon-containing intermediate film that contains the fluorine-containing silicon resin produced from a raw material of the inventive fluorine-containing silicon compound enables suppression of the reflection in any high-NA exposure condition of dry or liquid immersion; and thus enables an excellent pattern to be formed. Moreover, this enables the formation of a silicon-containing film usable as an excellent dry etching mask, between the photoresist film at the upper layer and the organic film at the lower layer. This silicon-containing film is particularly excellent in etching selectivity to the upper photoresist layer, so that the transformation of the upper resist layer can be inhibited during the dry etching of the silicon-containing film.

In addition, the above fluorine-containing silicon resin is also suitably used for a silicon-containing photoresist composition. The fluorine-containing silicon resin is weakly acid due to the structure thereof. Because of this, a silicon-containing photoresist composition that contains the fluorine-containing silicon resin of the present invention has high affinity with an alkaline developer used in the pattern formation of photoresist, and thus can inhibit the generation of defects due to an insufficient development in the pattern development. On the other hand, since this resin is not excessively acid, pattern collapse is not advanced due to an excess development. Thus, it is suitably used for a silicon-containing photoresist composition.

In the general formula (5-1), each $R^3$ independently represents a hydrogen atom or a monovalent organic group having 1 to 30 carbon atoms. More specifically, as $R^3$, a hydrogen atom, a methyl group, an ethyl group, a phenyl group, a hexyl group, a decyl group, a trifluoropropyl group, a vinyl group, a 2-(3,4-epoxycyclohexyl)ethyl group, a 3-glycidoxypropyl group, a 3-methacryloxypropyl group, a 3-(2-aminoethylamino)propyl group, a 3-aminopropyl group, a N-phenyl-3-aminopropyl group, a 3-chloropropyl group, a 3-mercaptopropyl group, a tolyl group, a xylyl group, a fluorophenyl group, a difluorophenyl group, a t-butoxyphenyl group, a phenethyl group, and a benzyl group are particularly preferable, but it is not limited thereto.

In the general formula (5-1), each $R^4$ independently represents a hydrocarbon group having 1 to 6 carbon atoms. More specifically, a methyl group, an ethyl group, a propyl group, an isopropyl group, a butyl group, a s-butyl group, a t-butyl group, an isobutyl group, a pentyl group, a hexyl group, a cyclohexyl group, a phenyl group, and an allyl group are particularly preferable, but it is not limited thereto.

In the general formula (5-1), m1 is an integer satisfying $0 \leq m1 \leq 3$, preferably 0, 1, or 2, particularly preferably 0 or 1.

Illustrative examples of the hydrolysable silicon compound represented by the general formula (5-1) include the following compounds, but it is not limited thereto.

Examples of tetraalkoxy silane include tetramethoxy silane, tetraethoxy silane, tetrapropoxy silane, tetraisopropoxy silane, etc.

Examples of trialkoxy silane include trimethoxy silane, triethoxy silane, tripropoxy silane, triisopropoxy silane, methyl trimethoxy silane, methyl triethoxy silane, methyl tripropoxy silane, methyl triisopropoxy silane, ethyl trimethoxy silane, ethyl triethoxy silane, ethyl tripropoxy silane, ethyl triisopropoxy silane, vinyl trimethoxy silane, vinyl triethoxy silane, vinyl tripropoxy silane, vinyl triisopropoxy silane, propyl trimethoxy silane, propyl triethoxy silane, propyl tripropoxy silane, propyl triisopropoxy silane, isopropyl trimethoxy silane, isopropyl triethoxy silane, isopropyl tripropoxy silane, isopropyl triisopropoxy silane, butyl trimethoxy silane, butyl triethoxy silane, butyl tripropoxy silane, butyl triisopropoxy silane, s-butyl trimethoxy silane, s-butyl triethoxy silane, s-butyl tripropoxy silane, s-butyl triisopropoxy silane, t-butyl trimethoxy silane, t-butyl triethoxy silane, t-butyl tripropoxy silane, isobutyl trimethoxy silane, isobutyl triethoxy silane, allyl trimethoxy silane, allyl triethoxy silane, cyclopropyl trimethoxy silane, cyclopropyl triethoxy silane, cyclopropyl tripropoxy silane, cyclopropyl triisopropoxy silane, cyclobutyl trimethoxy silane, cyclobutyl triethoxy silane, cyclobutyl tripropoxy silane, cyclobutyl triisopropoxy silane, cyclopentyl trimethoxy silane, cyclopentyl triethoxy silane, cyclopentyl tripropoxy silane, cyclopentyl triisopropoxy silane, cyclohexyl trimethoxy silane, cyclohexyl triethoxy silane, cyclohexyl tripropoxy silane, cyclohexyl triisopropoxy silane, cyclohexenyl trimethoxy silane, cyclohexenyl triethoxy silane, cyclohexenyl tripropoxy silane, cyclohexenyl triisopropoxy silane, cyclohexenylethyl trimethoxy silane, cyclohexenylethyl triethoxy silane, cyclohexenylethyl tripropoxy silane, cyclohexenylethyl triisopropoxy silane, cyclooctanyl trimethoxy silane, cyclooctanyl triethoxy silane, cyclooctanyl tripropoxy silane, cyclooctanyl triisopropoxy silane, cyclopentadienylpropyl trimethoxy silane, cyclopentadienylpropyl triethoxy silane, cyclopentadienylpropyl tripropoxy silane, cyclopentadienylpropyl triisopropoxy silane, bicycloheptenyl trimethoxy silane, bicycloheptenyl triethoxy silane, bicycloheptenyl tripropoxy silane, bicycloheptenyl triisopropoxy silane, bicycloheptyl trimethoxy silane, bicycloheptyl triethoxy silane, bicycloheptyl tripropoxy silane, bicycloheptyl triisopropoxy silane, adamantyl trimethoxy silane, adamantyl triethoxy silane, adamantyl tripropoxy silane, adamantyl triisopropoxy silane, phenyl trimethoxy silane, phenyl triethoxy silane, phenyl tripropoxy silane, phenyl triisopropoxy silane, benzyl trimethoxy silane, benzyl triethoxy silane, benzyl tripropoxy silane, benzyl triisopropoxy silane, tolyl trimethoxy silane, tolyl triethoxy silane, tolyl tripropoxy silane, tolyl triisopropoxy silane, phenethyl trimethoxy silane, phenethyl triethoxy silane, phenethyl tripropoxy silane, phenethyl triisopropoxy silane, naphthyl trimethoxy silane, naphthyl triethoxy silane, naphthyl tripropoxy silane, naphthyl triisopropoxy silane, etc.

Examples of dialkoxy silane include dimethyl dimethoxy silane, dimethyl diethoxy silane, methyl ethyl dimethoxy silane, methyl ethyl diethoxy silane, dimethyl dipropoxy silane, dimethyl diisopropoxy silane, diethyl dimethoxy silane, diethyl diethoxy silane, diethyl dipropoxy silane, diethyl diisopropoxy silane, dipropyl dimethoxy silane, dipropyl diethoxy silane, dipropyl dipropoxy silane, dipropyl diisopropoxy silane, diisopropyl dimethoxy silane, diisopropyl diethoxy silane, diisopropyl dipropoxy silane, diisopropyl diisopropoxy silane, dibutyl dimethoxy silane, dibutyl diethoxy silane, dibutyl dipropoxy silane, dibutyl diisopropoxy silane, di-s-butyl dimethoxy silane, di-s-butyl diethoxy silane, di-s-butyl dipropoxy silane, di-s-butyl diisopropoxy silane, di-t-butyl dimethoxy silane, di-t-butyl diethoxy silane, di-t-butyl dipropoxy silane, di-t-butyl diisopropoxy silane, dicyclopropyl dimethoxy silane, dicyclopropyl diethoxy silane, dicyclopropyl dipropoxy silane, dicyclopropyl diisopropoxy silane, dicyclobutyl dimethoxy silane, dicyclobutyl diethoxy silane, dicyclobutyl dipropoxy silane, dicyclobutyl diisopropoxy silane, dicyclopentyl dimethoxy silane, dicyclopentyl diethoxy silane, dicyclopentyl dipropoxy silane, dicyclopentyl diisopropoxy silane, dicyclohexyl dimethoxy silane, dicyclohexyl diethoxy silane, dicyclohexyl dipropoxy silane, dicyclohexyl diisopropoxy silane, dicyclohexenyl dimethoxy silane, dicyclohexenyl diethoxy silane, dicyclohexenyl dipropoxy silane, dicyclohexenyl diisopropoxy silane, dicyclohexenylethyl dimethoxy silane, dicyclohexenylethyl diethoxy silane, dicyclohexenylethyl dipropoxy silane, dicyclohexenylethyl diisopropoxy silane, dicyclooctanyl dimethoxy silane, dicyclooctanyl diethoxy silane, dicyclooctanyl dipropoxy silane, dicyclooctanyl diisopropoxy silane, dicyclopentadienylpropyl dimethoxy silane, dicyclopentadienylpropyl diethoxy silane, dicyclopentadienylpropyl dipropoxy silane, dicyclopentadienylpropyl diisopropoxy silane, bis(bicycloheptenyl) dimethoxy silane, bis(bicycloheptenyl) diethoxy silane, bis (bicycloheptenyl) dipropoxy silane, bis(bicycloheptenyl) diisopropoxy silane, bis(bicycloheptyl) dimethoxy silane, bis(bicycloheptyl) diethoxy silane, bis(bicycloheptyl) dipropoxy silane, bis(bicycloheptyl) diisopropoxy silane, bisadamantyl dimethoxy silane, bisadamantyl diethoxy silane, bisadamantyl dipropoxy silane, bisadamantyl diisopropoxy silane, diphenyl dimethoxy silane, diphenyl diethoxy silane, methyl phenyl dimethoxy silane, methyl phenyl diethoxy silane, diphenyl dipropoxy silane, diphenyl diisopropoxy silane, etc.

Examples of monoalkoxy silane include trimethyl methoxy silane, trimethyl ethoxy silane, dimethyl ethyl methoxy silane, dimethyl ethyl ethoxy silane, dimethyl phenyl methoxy silane, dimethyl phenyl ethoxy silane, dimethyl benzyl methoxy silane, dimethyl benzyl ethoxy silane, dimethyl phenethyl methoxy silane, dimethyl phenethyl ethoxy silane, etc.

Preferable examples include tetramethoxy silane, tetraethoxy silane, methyltrimethoxy silane, methyl triethoxy silane, ethyl trimethoxy silane, ethyl triethoxy silane, vinyl trimethoxy silane, vinyl triethoxy silane, propyl trimethoxy silane, propyl triethoxy silane, isopropyl trimethoxy silane, isopropyl triethoxy silane, butyl trimethoxy silane, butyl triethoxy silane, isobutyl trimethoxy silane, isobutyl triethoxy silane, allyl trimethoxy silane, allyl triethoxy silane, cyclopentyl trimethoxy silane, cyclopentyl triethoxy silane, cyclohexyl trimethoxy silane, cyclohexyl triethoxy silane, cyclohexenyl trimethoxy silane, cyclohexenyl triethoxy silane, phenyl trimethoxy silane, phenyl triethoxy silane, benzyl trimethoxy silane, benzyl triethoxy silane, phenethyl trimethoxy silane, phenethyl triethoxy silane, dimethyl dimethoxy silane, dimethyl diethoxy silane, diethyl dimethoxy silane, diethyl diethoxy silane, methyl ethyl dimethoxy silane, methyl ethyl diethoxy silane, dipropyl dimethoxy silane, dibutyl dimethoxy silane, methyl phenyl dimethoxy silane, methyl phenyl diethoxy silane, trimethyl methoxy silane, dimethyl ethyl methoxy silane, dimethyl phenyl methoxy silane, dimethyl benzyl methoxy silane, and dimethyl phenethyl methoxy silane.

In the general formula (5-2), U represents any element belonging to the group of III, IV, or V in the periodic table, except for carbon and silicon. Particularly preferable examples of U include boron, aluminum, gallium, yttrium, germanium, titanium, zirconium, hafnium, bismuth, tin, phosphorus, vanadium, arsenic, antimony, niobium, and tantalum.

The fluorine-containing silicon resin that contains the metal shown by U exhibits a higher etching speed as an intermediate film than the fluorine-containing silicon resin not containing the metal if the resin is applied to the intermediate film for multilayer lithography; and thus, it has advantage that the intermediate film capable of pattern transfer can be formed even if a thinned photoresist is used as an etching mask.

In the general formula (5-2), $R^5$ and $R^6$ independently represent a hydrogen atom or an organic group having 1 to 30 carbon atoms. As $R^5$ and $R^6$, more specifically, a hydrogen atom, a methyl group, an ethyl group, a propyl group, an isopropyl group, a butyl group, a s-butyl group, a t-butyl group, an isobutyl group, a pentyl group, a hexyl group, a cyclohexyl group, a phenyl group, an allyl group, a benzyl group, a phenethyl group, an icosanyl group, and a tricosanyl group are particularly preferable, but it is not limited thereto.

In the general formula (5-2), m2+m3+m4 is a number of valency determined by U, and each of m2, m3, and m4 is an integer of 0 or more. Typically, for example, when U is titanium, zirconium, hafnium, germanium, tin, or zinc, m2+m3+m4=4; when U is vanadium, niobium, or tantalum, m2+m3+m4=5; when U is phosphorus, arsenic, antimony, or bismuth, m2+m3+m4=3 or 5; and when U is boron, aluminum, gallium, yttrium, indium, or thallium, m2+m3+m4=3.

Illustrative examples of the reactive compound represented by the general formula (5-2) include the following compounds, but it is not limited thereto.

In the case that U is boron, examples include boron methoxide, boron ethoxide, boron propoxide, boron isopropoxide, boron butoxide, boron amyloxide, boron hexyloxide, boron cyclopentoxide, boron cyclohexyloxide, boron allyloxide, boron phenoxide, boron methoxyethoxide, boric acid, and boron oxide.

In the case that U is aluminum, examples include aluminum methoxide, aluminum ethoxide, aluminum propoxide, aluminum isopropoxide, aluminum butoxide, aluminum amyloxide, aluminum hexyloxide, aluminum cyclopentoxide, aluminum cyclohexyloxide, aluminum allyloxide, aluminum phenoxide, aluminum methoxyethoxide, aluminum ethoxyethoxide, aluminum dipropoxyethyl acetoacetate, aluminum dibutoxyethyl acetoacetate, aluminum propoxy bisethyl acetoacetate, aluminum butoxy bisethyl acetoacetate, aluminum 2,4-pentanedionate, and aluminum 2,2,6,6-tetramethyl-3,5-heptanedionate.

In the case that U is gallium, examples include gallium methoxide, gallium ethoxide, gallium propoxide, gallium isopropoxide, gallium butoxide, gallium amyloxide, gallium hexyloxide, gallium cyclopentoxide, gallium cyclohexyloxide, gallium allyloxide, gallium phenoxide, gallium methoxyethoxide, gallium ethoxyethoxide, gallium dipropoxyethyl acetoacetate, gallium dibutoxyethyl acetoacetate, gallium propoxy bisethyl acetoacetate, gallium butoxy bisethyl acetoacetate, gallium 2,4-pentanedionate, and gallium 2,2,6,6-tetramethyl-3,5-heptanedionate.

In the case that U is yttrium, examples include yttrium methoxide, yttrium ethoxide, yttrium propoxide, yttrium isopropoxide, yttrium butoxide, yttrium amyloxide, yttrium hexyloxide, yttrium cyclopentoxide, yttrium cyclohexyloxide, yttrium allyloxide, yttrium phenoxide, yttrium methoxyethoxide, yttrium ethoxyethoxide, yttrium dipropoxyethyl acetoacetate, yttrium dibutoxyethyl acetoacetate, yttrium propoxy bisethyl acetoacetate, yttrium butoxy bisethyl acetoacetate, yttrium 2,4-pentanedionate, and yttrium 2,2,6,6-tetramethyl-3,5-heptanedionate.

In the case that U is germanium, examples include germanium methoxide, germanium ethoxide, germanium propoxide, germanium isopropoxide, germanium butoxide, germanium amyloxide, germanium hexyloxide, germanium cyclopentoxide, germanium cyclohexyloxide, germanium allyloxide, germanium phenoxide, germanium methoxyethoxide, and germanium ethoxyethoxide.

In the case that U is titanium, examples include titanium methoxide, titanium ethoxide, titanium propoxide, titanium isopropoxide, titanium butoxide, titanium amyloxide, titanium hexyloxide, titanium cyclopentoxide, titanium cyclohexyloxide, titanium allyloxide, titanium phenoxide, titanium methoxyethoxide, titanium ethoxyethoxide, titanium dipropoxy bisethyl acetoacetate, titanium dibutoxy bisethyl acetoacetate, titanium dipropoxy bis-2,4-pentanedionate, and titanium dibutoxy bis-2,4-pentanedionate.

In the case that U is zirconium, examples include zirconium methoxide, zirconium ethoxide, zirconium propoxide, zirconium isopropoxide, zirconium butoxide, zirconium phenoxide, zirconium dibutoxide bis(2,4-pentanedionate), and zirconium dipropoxide bis(2,2,6,6-tetramethyl-3,5-heptanedionate).

In the case that U is hafnium, examples include hafnium methoxide, hafnium ethoxide, hafnium propoxide, hafnium isopropoxide, hafnium butoxide, hafnium amyloxide, hafnium hexyloxide, hafnium cyclopentoxide, hafnium cyclohexyloxide, hafnium allyloxide, hafnium phenoxide, hafnium methoxyethoxide, hafnium ethoxyethoxide, hafnium dipropoxybisethyl acetoacetate, hafnium dibutoxybisethyl acetoacetate, hafnium dipropoxybis-2,4-pentanedionate, and hafnium dibutoxybis-2,4-pentanedionate.

In the case that U is bismuth, examples include bismuth methoxide, bismuth ethoxide, bismuth isopropoxide, bismuth butoxide, and bismuth phenoxide.

In the case that U is tin, examples include tin methoxide, tin ethoxide, tin isopropoxide, tin butoxide, tin phenoxide, tin methoxyethoxide, tin ethoxyethoxide, tin 2,4-pentanedionate, and tin 2,2,6,6-tetramethyl-3,5-heptanedionate.

In the case that U is phosphorus, examples include trimethylphosphite, triethylphosphite, triisopropylphosphite, trimethylphosphate, triethyl-phosphate, tripropylphosphate, diphosphorous pentaoxide, phosphoric acid, phosphorus acid, and polyphosphoric acid.

In the case that U is vanadium, examples include vanadium oxide bis(2,4-pentanedionate), vanadium 2,4-pentanedionate, vanadium tributoxide oxide, and vanadium triisopropoxide oxide.

In the case that U is arsenic, examples include arsenic methoxide, arsenic ethoxide, arsenic isopropoxide, arsenic butoxide, and arsenic phenoxide.

In the case that U is antimony, examples include antimony methoxide, antimony ethoxide, antimony isopropoxide, antimony butoxide, antimony phenoxide, antimony acetate, and antimony propionate.

In the case that U is niobium, examples include niobium methoxide, niobium ethoxide, niobium isopropoxide, niobium butoxide, and niobium phenoxide.

In the case that U is tantalum, examples include tantalum methoxide, tantalum ethoxide, tantalum isopropoxide, tantalum butoxide, and tantalum phenoxide.

One or more fluorine-containing silicon compounds represented by the general formula (1) and one or more compounds selected from the group consisting of the hydrolysable silicon compound represented by the general formula (5-1) and the reactive compound represented by the general formula (5-2) like this are selected and mixed before or during the reaction to be used as the starting material for producing the fluorine-containing silicon resin.

Preferable producing conditions are exemplified by the following, although the condition is not limited thereto. The fluorine-containing silicon resin can be produced by hydrolysis condensation of one or more fluorine-containing silicon compounds represented by the general formula (1) with one or more compounds selected from the group consisting of the hydrolysable silicon compound represented by the general formula (5-1) and the reactive compound represented by the general formula (5-2) (hereinafter, referred to as "monomer"), using one or more compounds selected from acids, preferably inorganic acid and sulfonic acid derivative (aliphatic sulfonic acid and aromatic sulfonic acid), as a catalyst.

Illustrative examples of the acid catalyst used for the reaction include hydrofluoric acid, hydrochloric acid, hydrobromic acid, sulfuric acid, nitric acid, perchloric acid, phosphoric acid, methanesulfonic acid, benzenesulfonic acid, and toluenesulfonic acid. The amount of the catalyst to be used is preferably in the range of $1 \times 10^{-6}$ to 10 mol, more preferably $1 \times 10^{-5}$ to 5 mol, much more preferably $1 \times 10^{-4}$ to 1 mol per 1 mol of the monomers.

The amount of water to be added for obtaining the fluorine-containing silicon resin by hydrolysis condensation of these monomers is preferably in the range of 0.01 to 100 mol, more preferably 0.05 to 50 mol, much more preferably 0.1 to 30 mol per 1 mol of a hydrolysable substituent bonded to the monomers. If the amount is 100 mol or less, a reaction device does not become excessively large, resulting in economical.

As an operation manner, for example, the monomers are added to a catalyst aqueous solution to start hydrolysis condensation reaction. In the manner, an organic solvent may be added to the catalyst aqueous solution, the monomers may be diluted with an organic solvent, or both may be performed. The reaction temperature is preferably in the range of 0 to 100° C., and more preferably 5 to 80° C. In particular, a method including maintaining the temperature at 5 to 80° C. while the monomers are added dropwise, and then aging the mixture at 20 to 80° C. is preferable.

Illustrative examples of the organic solvent that can be added to the catalyst aqueous solution, or can dilute the monomers, include methanol, ethanol, 1-propanol, 2-propanol, 1-butanol, 2-butanol, 2-methyl-1-propanol, acetone, acetonitrile, tetrahydrofuran, toluene, hexane, ethyl acetate, cyclohexanone, methylisobutyl ketone, butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, propyleneglycoldimethyl ether, diethyleneglycoldimethyl ether, propyleneglycolmonomethyl ether acetate, propyleneglycolmonoethyl ether acetate, ethyl pyruvate, butyl acetate, methyl 3-methoxypropionate, ethyl 3-ethoxypropionate, t-butyl acetate, t-butyl propionate, propyleneglycolmono-t-butyl ether acetate, γ-butyrolactone, and mixture thereof.

Among them, water-soluble solvents are preferable. Illustrative examples thereof include alcohols such as methanol, ethanol, 1-propanol, and 2-propanol; polyhydric alcohols such as ethylene glycol and propylene glycol; polyhydric alcohol condensate derivatives such as butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, and ethyleneglycolmonopropyl ether; acetone; acetonitrile; tetrahydrofuran, etc. Particularly preferable is a solvent with a boiling point of 100° C. or less.

The amount of the organic solvent to be used is preferably in the range of 0 to 1,000 mL, and particularly preferably 0 to 500 mL per 1 mol of the monomers. If the amount of the organic solvent is in such a range, an excessively large reaction vessel is not required, and thus the reaction can be performed economically.

Thereafter, if necessary, neutralization reaction of the catalyst is carried out, and alcohol produced by hydrolysis condensation reaction is removed under reduced pressure to obtain a reaction mixture aqueous solution. The amount of an alkaline substance to be used for neutralization is preferably 0.1 to 2 equivalent with respect to an acid used as the catalyst. The alkaline substance may be any substance so long as it shows basicity in water.

Subsequently, it is preferable that by-products such as alcohol produced by hydrolysis condensation reaction be removed from the reaction mixture. The temperature for heating the reaction mixture is preferably in the range of 0 to 100° C., more preferably 10 to 90° C., and much more preferably 15 to 80° C. though it is depending on the kinds of the added organic solvent and the alcohol produced by the reaction. Degree of vacuum in this operation is preferably atmospheric pressure or less, more preferably 80 kPa or less in the absolute pressure, and much more preferably 50 kPa or less in the absolute pressure though it is depending on the kinds of the organic solvent and the alcohol to be removed, an exhausting equipment, a condensation equipment, and heating temperature. Although it is difficult to know exactly the amount of the alcohol removed, it is preferable that about 80% by mass or more of the produced alcohol and so forth be removed.

Next, the acid catalyst used for hydrolysis condensation may be removed from the reaction mixture. A method for removing the acid catalyst may be to mix water and the fluorine-containing silicon resin, and then extract the fluorine-containing silicon resin by an organic solvent. As the organic solvent, those that can dissolve the fluorine-containing silicon resin, and be separated into two layers when mixed with water is preferably used. Illustrative examples thereof include methanol, ethanol, 1-propanol, 2-propanol, 1-butanol, 2-butanol, 2-methyl-1-propanol, acetone, tetrahydrofuran, toluene, hexane, ethyl acetate, cyclohexanone, methylisobutyl ketone, butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, ethyleneglycolmonopropyl ether, propyleneglycoldimethyl ether, diethyleneglycoldimethyl ether, propyleneglycolmonomethyl ether acetate, propyleneglycolmonoethyl ether acetate, ethyl pyruvate, butyl acetate, methyl 3-methoxypropionate, ethyl 3-ethoxypropionate, t-butyl acetate, t-butyl propionate, propyleneglycolmono-t-butyl ether acetate, γ-butyrolactone, cyclopentylmethyl ether, etc., and mixture thereof.

Moreover, a mixture of a water-soluble organic solvent and a slightly water-soluble organic solvent can also be used. Preferable examples thereof include methanol+ethyl acetate mixture, ethanol+ethyl acetate mixture, 1-propanol+ethyl acetate mixture, 2-propanol+ethyl acetate mixture, butanediolmonomethyl ether+ethyl acetate mixture, propyleneglycolmonomethyl ether+ethyl acetate mixture, ethyleneglycolmonomethyl ether+ethyl acetate mixture, butanediolmonoethyl ether+ethyl acetate mixture, propyleneglycolmonoethyl ether+ethyl acetate mixture, ethyleneglycolmonoethyl ether+ethyl acetate mixture, butanediolmonopropyl ether+ethyl acetate mixture, propyleneglycolmonopropyl ether+ethyl acetate mixture, ethyleneglycolmonopropyl ether+ethyl acetate mixture, methanol+methylisobutyl ketone mixture, ethanol+methylisobutyl ketone mixture, 1-propanol+methylisobutyl ketone mixture, 2-propanol+methylisobutyl ketone mixture, propyleneglycolmonomethyl ether+methylisobutyl ketone mixture, ethyleneglycolmonomethyl ether+methylisobutyl ketone mixture, propyleneglycolmonoethyl ether+methylisobutyl ketone mixture, ethyleneglycolmonoethyl ether+methylisobutyl ketone mixture, propyleneglycolmonopropyl ether+methylisobutyl ketone mixture, ethyleneglycolmonopropyl ether+methylisobutyl ketone mixture, methanol+cyclopentylmethyl ether mixture, ethanol+cyclopentylmethyl ether mixture, 1-propanol+cyclopentylmethyl ether mixture, 2-propanol+cyclopentylmethyl ether mixture, propyleneglycolmonomethyl ether+cyclopentylmethyl ether mixture, ethyleneglycolmonomethyl ether+cyclopentylmethyl ether mixture, propyleneglycolmonoethyl ether+cyclopentylmethyl ether mixture, ethyleneglycolmonoethyl ether+cyclopentylmethyl ether mixture, propyleneglycolmonopropyl ether+cyclopentylmethyl ether mixture, ethyleneglycolmonopropyl ether+cyclopentylmethyl ether mixture, methanol+propyleneglycolmethyl ether acetate mixture, ethanol+propyleneglycolmethyl ether acetate mixture, 1-propanol+propyleneglycolmethyl ether acetate mixture, 2-propanol+propyleneglycolmethyl ether acetate mixture, propyleneglycolmonomethyl ether+propyleneglycolmethyl ether acetate mixture, ethyleneglycolmonomethyl ether+propyleneglycolmethyl ether acetate mixture, propyleneglycolmonoethyl ether+propyleneglycolmethyl ether acetate mixture, ethyleneglycolmonoethyl ether+propyleneglycolmethyl ether acetate mixture, propyleneglycolmonopropyl ether+propyleneglycolmethyl ether acetate mixture, ethyleneglycolmonopropyl ether+propyleneglycolmethyl ether acetate mixture, etc., but it is not limited thereto.

The mixing ratio of the water-soluble organic solvent and the slightly water-soluble organic solvent is appropriately determined. The amount of the water-soluble organic solvent is preferably in the range of 0.1 to 1,000 parts by mass, more preferably 1 to 500 parts by mass, and much more preferably 2 to 100 parts by mass, based on 100 parts by mass of the slightly water-soluble organic solvent.

Subsequently, the reaction mixture may be washed with neutral water to remove water-soluble impurities such as the acid catalyst. The neutral water may be water called deionized water or ultrapure water. The amount of water for washing is preferably in the range of 0.01 to 100 L, more preferably 0.05 to 50 L, and much more preferably 0.1 to 5 L per 1 L of the fluorine-containing silicon resin solution. The washing may be carried out in such a way that the both the fluorine-containing silicon resin solution and water for washing are mixed in a vessel by stirring, and then settled to separate a water layer. The number of washing may be one or more, and preferably about 1 to 5 times because washing of 10 times or more is not worth to have full effects thereof.

Other methods for removing the acid catalyst include a method using an ion-exchange resin, and a method for removing an acid catalyst after neutralization with an epoxy compound such as ethylene oxide and propylene oxide. These methods can be appropriately selected according to the acid catalyst used in the reaction.

In the catalyst removal operation, the acid catalyst used in the reaction is preferably removed until the amount thereof is decreased to about 10% by mass or less, preferably 5% by mass or less of the amount added into the fluorine-containing silicon resin solution at the start of the reaction.

In the water-washing, a part of the fluorine-containing silicon resin may escape into a water layer, whereby substantially the same effect as fractionation operation is obtained. Therefore, the number of washing and the amount of water for washing may be appropriately determined in view of effects of catalyst removal and fractionation.

A final solvent is then added to the fluorine-containing silicon resin solution in either case that the acid catalyst remains therein or has been removed therefrom, and solvent-exchange is thereby performed under reduced pressure to obtain a desired solution of the fluorine-containing silicon resin. The temperature during the solvent-exchange is preferably in the range of 0 to 100° C., more preferably 10 to 90° C., and much more preferably 15 to 80° C. though it is depending on the kinds of the reaction solvent and the extraction solvent to be removed. Degree of vacuum in this operation is preferably atmospheric pressure or less, more preferably 80 kPa or less in the absolute pressure, and much more preferably 50 kPa or less in the absolute pressure though it is depending on the kinds of the solvents to be removed, an exhausting equipment, condensation equipment, and heating temperature.

In this operation, sometimes the fluorine-containing silicon resin may become unstable because the solvent was exchanged. This occurs due to incompatibility of the fluorine-containing silicon resin with the final solvent. Thus, in order to prevent this problem, a later-described stabilizer may be added thereto. The amount thereof to be added is preferably in the range of 0 to 25 parts by mass, more preferably 0 to 15 parts by mass, and much more preferably 0 to 5 parts by mass, or 0.5 part by mass or more when it is added, based on 100 parts by mass of the fluorine-containing silicon resin contained in the solution before the solvent-exchange. If necessary, a stabilizer may be added to the solution before the solvent-exchange operation.

The fluorine-containing silicon resin solution is preferably made the state of solution with proper concentration. For example, the concentration is preferably in the range of 0.1 to 20% by mass. If the concentration is 20% by mass or less, the fluorine-containing silicon resin can be prevented from becoming insoluble in the organic solvent due to the progress of condensation reaction. In addition, if the concentration is 0.1% by mass or more, the amount of the solvent does not become excessively large, and therefore it is economical.

Preferable examples of the final solvent added to the fluorine-containing silicon resin solution include alcohol solvents, and particularly monoalkyl ether derivatives of ethylene glycol, diethylene glycol, triethylene glycol, propylene glycol, dipropylene glycol, butanediol, or the like. Illustrative examples thereof include butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, ethyleneglycolmonopropyl ether, etc.

In addition, if these solvents are a main solvent, a non-alcoholic solvent may be added thereinto as an adjuvant solvent. Illustrative examples of this adjuvant solvent include acetone, tetrahydrofuran, toluene, hexane, ethyl acetate, cyclohexanone, methylisobutyl ketone, propyleneglycoldimethyl ether, diethyleneglycoldimethyl ether, propyleneglycolmonomethyl ether acetate, propyleneglycolmonoethyl ether acetate, ethyl pyruvate, butyl acetate, methyl 3-methoxypropionate, ethyl 3-ethoxypropionate, t-butyl acetate, t-butyl propionate, propyleneglycolmono-t-butyl ether acetate, γ-butyrolactone, cyclopentylmethyl ether, etc.

As an alternative operation manner, water or a water-containing organic solvent may be added to the monomers or an organic solution of the monomers to start hydrolysis reaction. In the manner, the catalyst may be added to the monomers or the organic solution of the monomers, or may be added to the water or the water-containing organic solvent. The reaction temperature is preferably in the range of 0 to 100° C., more preferably 10 to 80° C. In particular, a method including heating the mixture at 10 to 50° C. while water is added dropwise, and then increasing the temperature to 20 to 80° C. to age the mixture is preferable.

In the case that the organic solvent is used, water-soluble solvent is preferable, and illustrative examples thereof include alcohols such as methanol, ethanol, 1-propanol, 2-propanol, 1-butanol, 2-butanol, and 2-methyl-1-propanol; polyhydric alcohol condensate derivatives such as butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, ethyleneglycolmonopropyl ether, propyleneglycoldimethyl ether, diethyleneglycoldimethyl ether, propyleneglycolmonomethyl ether acetate, propyleneglycolmonoethyl ether acetate, and propyleneglycolmonopropyl ether; acetone; tetrahydrofuran; acetonitrile, etc., and a mixture thereof.

The amount of the organic solvent to be used may be the same amount as above. Subsequently, the obtained reaction mixture may be treated in the same manner as mentioned above to obtain the fluorine-containing silicon resin.

The weight average molecular weight of the fluorine-containing silicon resin thus obtained can be adjusted not only by selecting monomers, but also controlling reaction conditions in the polymerization. The weight average molecular weight is preferably 100,000 or less, more preferably in the range of 200 to 50,000, and much more preferably 300 to 30,000. If the weight average molecular weight is 100,000 or less, generation of foreign matters and coating spots can be suppressed.

Incidentally, the above weight average molecular weight is obtained as the data in terms of polystyrene, by means of gel-permeation chromatography (GPC) using refractive index (RI) detector as a detector and polystyrene as a reference material.

To ensure stability of the obtained fluorine-containing silicon resin, a monovalent, divalent or more polyvalent organic acid having 1 to 30 carbon atoms may be added as a stabilizer. Preferable examples of the organic acid to be added include formic acid, acetic acid, propionic acid, butanoic acid, pentanoic acid, hexanoic acid, heptanoic acid, octanoic acid, nonanoic acid, decanoic acid, oleic acid, stearic acid, linoleic acid, linolenic acid, benzoic acid, phthalic acid, isophthalic acid, terephthalic acid, salicylic acid, trifluoroacetic acid, monochloroacetic acid, dichloroacetic acid, trichloroacetic acid, oxalic acid, malonic acid, methylmalonic acid, ethylmalonic acid, propylmalonic acid, butylmalonic acid, dimethylmalonic acid, diethylmalonic acid, succinic acid, methylsuccinic acid, glutaric acid, adipic acid, itaconic acid, maleic acid, fumaric acid, citraconic acid, citric acid, etc. Especially, oxalic acid, maleic acid, formic acid, acetic acid, propionic acid, citric acid, and the like are preferable. To keep stability, two or more organic acids may be used as a mixture.

When the fluorine-containing silicon resin is used for a resin contained in a composition for forming a silicon-containing intermediate film or a silicon-containing photoresist composition, the amount of inorganic acid to be added is preferably 0.001 to 25 parts by mass, more preferably 0.01 to 15 parts by mass, and much more preferably 0.1 to 5 parts by mass, based on 100 parts by mass of the fluorine-containing silicon resin contained in these compositions. Alternatively, the organic acid is preferably added such that pH of the composition becomes preferably 0 pH 7, more preferably 0.3 pH 6.5, and much more preferably 0.5 pH 6.

EXAMPLES

Hereinafter, the present invention will be specifically described with reference to Examples and Comparative Examples, but the present invention is not restricted thereto.

The fluorine-containing silicon compound of the present invention was synthesized in the following manner.

Example 1-1

Synthesis 1 of
2,2-diethoxy-6,6-bis(trifluoromethyl)oxasilin (1A)

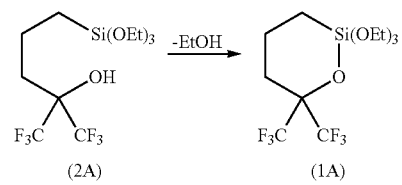

(2A)  (1A)

Into a flask were put 93.1 g of 1,1,1-trifluoro-5-(triethoxysilyl)-2-(trifluoromethyl)-2-pentanol (2A) and 50 g of toluene, and the flask was heated to totally reflux for 30 minutes. Then, components with low boiling point were gently distilled off over 20 hours. After cooling, the resulting component was purified by distillation under reduced pressure to obtain 65.3 g of 2,2-diethoxy-6,6-bis(trifluoromethyl)oxasilin (1A), with a boiling point of 74° C./1,100 Pa.

With respect to the obtained product, Infrared absorption (IR) spectrum and nuclear magnetic resonance ($^1$H-NMR, $^{13}$C-NMR, and $^{19}$F-NMR) spectra were measured, and the results are shown below.

IR (D-ATR): ν=2980, 2935, 2894, 1451, 1390, 1331, 1307, 1279, 1255, 1213, 1186, 1169, 1132, 1106, 1073, 1002, 956, 912, 875, 818, 798, 776, 711, 672 cm$^{-1}$ $^1$H-NMR (600 MHz, CDCl$_3$): δ=0.80 (2H, t, J=7.0 Hz), 1.23 (6H, t, J=7.0 Hz), 1.92-2.02 (4H, m), 3.85 (4H, q, J=7.0 Hz)

$^{13}$C-NMR (150 MHz, CDCl$_3$): δ=7.41, 17.01, 17.77, 27.02, 58.90, 78.82 (sep, J=29 Hz), 123.13 (q, J=287 Hz)

$^{19}$F-NMR (565 MHz, CDCl$_3$): δ=−78.81 (6F, s)

Example 1-2

Synthesis 2 of 2,2-diethoxy-6,6-bis(trifluoromethyl)oxasilin (1A)

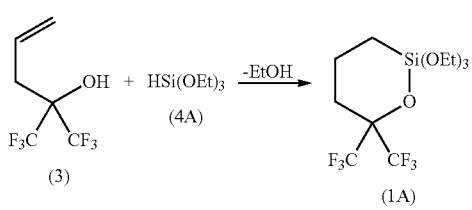

A mixture containing 208 g of 1,1,1-trifluoro-2-(trifluoromethyl)-4-penten-2-ol (3), 1.3 g of a toluene solution of platinum-1,3-divinyl-1,1,3,3-tetramethyldisiloxane complex (platinum content: 3% by mass), and 200 g of heptane was heated at about 100° C., and 172 g of triethoxy silane (4A) was added dropwise thereto over 20 hours while distilling off ethanol produced by the reaction. The heating was performed until the distillation of ethanol was completed, followed by cooling. Then, the resulting component was purified by distillation under reduced pressure to obtain 196 g of 2,2-diethoxy-6,6-bis(trifluoromethyl)oxasilin (1A), with a boiling point of 74° C./1,100 Pa.

With respect to the obtained product, Infrared absorption (IR) spectrum and nuclear magnetic resonance ($^1$H-NMR, $^{13}$C-NMR, and $^{19}$F-NMR) spectra were measured, and the results are shown below.

IR (D-ATR): ν=2980, 2935, 2894, 1451, 1390, 1331, 1307, 1279, 1255, 1213, 1186, 1169, 1132, 1106, 1073, 1002, 956, 912, 875, 818, 798, 776, 711, 672 cm$^{-1}$ $^1$H-NMR (600 MHz, CDCl$_3$): δ=0.80 (2H, t, J=7.0 Hz), 1.23 (6H, t, J=7.0 Hz), 1.92-2.02 (4H, m), 3.85 (4H, q, J=7.0 Hz)

$^{13}$C-NMR (150 MHz, CDCl$_3$): δ=7.41, 17.01, 17.77, 27.02, 58.90, 78.82 (sep, J=29 Hz), 123.13 (q, J=287 Hz)

$^{19}$F-NMR (565 MHz, CDCl$_3$): δ=−78.81 (6F, s)

Example 1-3

Synthesis of 2,2-dimethoxy-6,6-bis(trifluoromethyl)oxasilin (1B)

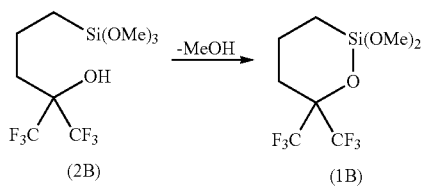

2,2-dimethoxy-6,6-bis(trifluoromethyl)oxasilin (1B) was obtained in the same manner as in Example 1, except for changing the raw material to 1,1,1-trifluoro-5-(trimethoxysilyl)-2-(trifluoromethyl)-2-pentanol (2B).

Example 1-4

Synthesis of 2-ethoxy-2-methyl-6,6-bis(trifluoromethyl)oxasilin (1C)

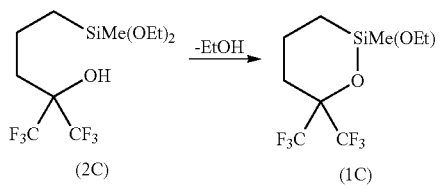

2-ethoxy-2-methyl-6,6-bis(trifluoromethyl)oxasilin (1C) was obtained in the same manner as in Example 1, except for changing the raw material to 1,1,1-trifluoro-5-(diethoxymethylsilyl)-2-(trifluoromethyl)-2-pentanol (2C).

Example 1-5

Synthesis of 2-methoxy-2-phenyl-6,6-bis(trifluoromethyl)oxasilin (1D)

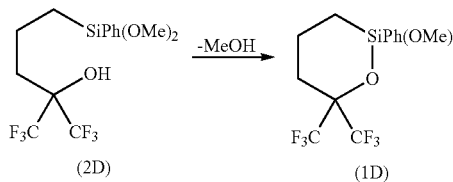

2-methoxy-2-phenyl-6,6-bis(trifluoromethyl) oxasilin (1D) was obtained in the same manner as in Example 1, except for changing the raw material to 1,1,1-trifluoro-5-(dimethoxyphenylsilyl)-2-(trifluoromethyl)-2-pentanol (2D)

Fluorine-containing silicon resins were produced by using the fluorine-containing silicon compounds synthesized in Examples 1-1 to 1-5 by the producing method of the present invention.

Example 2-1

Synthesis of Polymer-1

To a mixture containing 120 g of ethanol, 1 g of 70% nitric acid, and 60 g of deionized water was added a mixture containing 8.2 g of 2,2-diethoxy-6,6-bis(trifluoromethyl)oxasilin (1A), 84.2 g of tetraethoxy silane, 3.4 g of methyl trimethoxy silane, and 10.0 g of phenyl trimethoxy silane, and the resulting mixture was maintained at 40° C. for 12 hours to perform hydrolysis condensation. After completion of the reaction, 400 g of propyleneglycolmonoethyl ether (PGEE) was added thereto, and a by-produced alcohol and excess water were distilled off under reduced pressure to obtain 400 g of a PGEE solution of Polymer-1 (polymer concentration: 10%) shown by the following average composition formula. The molecular weight of the Polymer-1 was measured in terms of polystyrene by GPC analysis, consequently finding Mw=2,900 and dispersibility Mw/Mn=2.12.

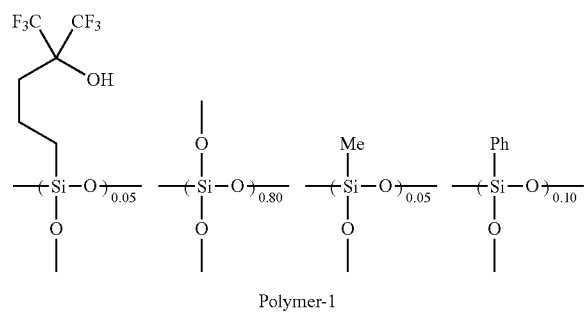

Polymer-1

Example 2-2

Synthesis of Polymer-2

To a mixture containing 120 g of ethanol, 1.8 g of phosphorus pentaoxide, 1 g of 70% nitric acid, and 60 g of deionized water was added a mixture containing 8.5 g of 2,2-diethoxy-6,6-bis(trifluoromethyl)oxasilin (1A), 81.3 g of tetraethoxy silane, 10.3 g of phenyl trimethoxy silane, and 2.7 g of trimethyl borate, and the resulting mixture was maintained at 40° C. for 12 hours to perform hydrolysis condensation. After completion of the reaction, 400 g of PGEE was added thereto, and a by-produced alcohol and excess water were distilled off under reduced pressure to obtain 400 g of a PGEE solution of Polymer-2 (polymer concentration: 10%) shown by the following average composition formula. The molecular weight of the Polymer-2 was measured in terms of polystyrene, consequently finding Mw=3,100 and dispersibility Mw/Mn=2.23.

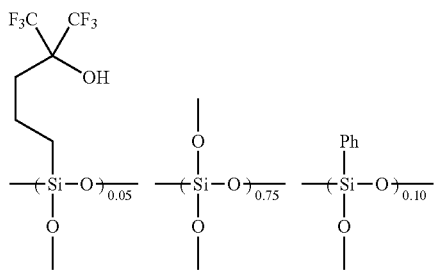

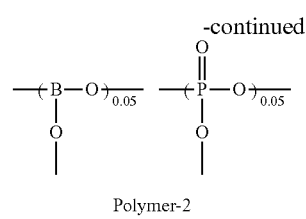

Polymer-2

Examples 2-3 to 2-5

Synthesis of Polymer-3 to Polymer-5

Polymer-3 to Polymer-5 were obtained by synthesizing the fluorine-containing silicon resin in the same manner as in Example 2-1, except for using, in place of 2,2-diethoxy-6,6-bis(trifluoromethyl)oxasilin (1A), 2,2-dimethoxy-6,6-bis(trifluoromethyl)oxasilin (1B), 2-ethoxy-2-methyl-6,6-bis(trifluoromethyl)oxasilin (1C), or 2-methoxy-2-phenyl-6,6-bis(trifluoromethyl)oxasilin (1D), respectively.

As shown in Examples 1-1 to 1-5 and Examples 2-1 to 2-5, it was confirmed that the fluorine-containing silicon compound of the present invention can be easily produced, and is useful as a raw material monomer of the fluorine-containing silicon resin produced by hydrolysis condensation.

[Storage Stability Test]

The purity of 2,2-diethoxy-6,6-bis(trifluoromethyl)oxasilin (1A) synthesized in Example 1-1 right after purification by distillation (purity before storage) was measured by gas chromatography flame ionization detector (GC-FID). Similarly, the purity (purity before storage) of the conventional fluorine-containing silicon compound, 1,1,1-trifluoro-5-(triethoxysilyl)-2-(trifluoromethyl)-2-pentanol (i.e., compound represented by the formula (6)), (Comparative example 1) was measured by GC-FID. Then, these compounds were stored at room temperature for 5 months under nitrogen atmosphere, and purities after storage were measured. As a result, the conventional fluorine-containing silicon compound, 1,1,1-trifluoro-5-(triethoxysilyl)-2-(trifluoromethyl)-2-pentanol (Comparative example 1) showed a purity before storage of 93.2% and a purity after storage of 57.8%, while the inventive fluorine-containing silicon compound, 2,2-diethoxy-6,6-bis(trifluoromethyl)oxasilin (1A) (Example 1-1) showed a purity before storage of 98.5% and a purity after storage of 98.8%.

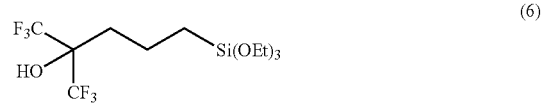

(6)

From the above results, it was revealed that the fluorine-containing silicon compound of the present invention has a significantly improved storage stability, compared with the conventional fluorine-containing silicon compound used for the same application, which indicates high industrial value of the inventive compound.

It should be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A fluorine-containing silicon compound represented by the general formula (1),

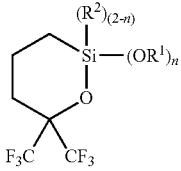
(1)

wherein each $R^1$ independently represents a hydrocarbon group having 1 to 6 carbon atoms; each $R^2$ independently represents a hydrogen atom or a hydrocarbon group having 1 to 6 carbon atoms; and n is an integer satisfying $0 \le n \le 2$.

2. The fluorine-containing silicon compound according to claim 1, wherein the fluorine-containing silicon compound is used as a raw material of a resin contained in a composition for forming a silicon-containing intermediate film or a silicon-containing photoresist composition.

3. A method for producing a fluorine-containing silicon compound according to claim 1, comprising subjecting a fluorine-containing silicon compound represented by the general formula (2) to intramolecular condensation,

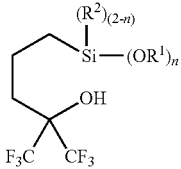
(2)

wherein each $R^1$ independently represents a hydrocarbon group having 1 to 6 carbon atoms; each $R^2$ independently represents a hydrogen atom or a hydrocarbon groups having 1 to 6 carbon atoms; and n is an integer satisfying $0 \le n \le 2$.

4. A method for producing a fluorine-containing silicon compound according to claim 2, comprising subjecting a fluorine-containing silicon compound represented by the general formula (2) to intramolecular condensation,

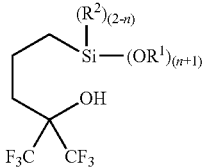
(2)

wherein each $R^1$ independently represents a hydrocarbon group having 1 to 6 carbon atoms; each $R^2$ independently represents a hydrogen atom or a hydrocarbon groups having 1 to 6 carbon atoms; and n is an integer satisfying $0 \le n \le 2$.

5. A method for producing a fluorine-containing silicon compound according to claim 1, comprising reacting a fluorine-containing compound represented by the formula (3) with a silicon compound represented by the general formula (4),

wherein each $R^1$ independently represents a hydrocarbon group having 1 to 6 carbon atoms; each $R^2$ independently represents a hydrogen atom or a hydrocarbon groups having 1 to 6 carbon atoms; and n is an integer satisfying $0 \le n \le 2$.

6. A method for producing a fluorine-containing silicon compound according to claim 2, comprising reacting a fluorine-containing compound represented by the formula (3) with a silicon compound represented by the general formula (4),

wherein each $R^1$ independently represents a hydrocarbon group having 1 to 6 carbon atoms; each $R^2$ independently represents a hydrogen atom or a hydrocarbon groups having 1 to 6 carbon atoms; and n is an integer satisfying $0 \le n \le 2$.

7. A method for producing a fluorine-containing silicon resin, comprising hydrolysis condensation of one or more compounds selected from the group consisting of a hydrolysable silicon compound represented by the general formula (5-1) and a reactive compound represented by the general formula (5-2) with one or more fluorine-containing silicon compounds according to claim 1,

(5-1)

(5-2)

wherein each $R^3$ independently represents a hydrogen atom or a monovalent organic group having 1 to 30 carbon atoms; each $R^4$ independently represents a hydrocarbon group having 1 to 6 carbon atoms; m1 is an integer satisfying $0 \le m1 \le 3$; $R^5$ and $R^6$ independently represent a hydrogen atom or an organic group having 1 to 30 carbon atoms; U represents any element belonging to the group of III, IV, or V in the periodic table, except for carbon and silicon; m2+m3+m4 is a number of valency determined by U; and each of m2, m3, and m4 is an integer of 0 or more.

8. A method for producing a fluorine-containing silicon resin, comprising hydrolysis condensation of one or more compounds selected from the group consisting of a hydrolysable silicon compound represented by the general formula (5-1) and a reactive compound represented by the general formula (5-2) with one or more fluorine-containing silicon compounds according to claim 2, $$R^3_{m1}Si(OR^4)_{(4-m1)} \quad (5\text{-}1)$$

$$U(OR^5)_{m2}(OR^6)_{m3}(O)_{m4/2} \quad (5\text{-}2)$$

wherein each $R^3$ independently represents a hydrogen atom or a monovalent organic group having 1 to 30 carbon atoms; each $R^4$ independently represents a hydrocarbon group having 1 to 6 carbon atoms; m1 is an integer satisfying $0 \leq m1 \leq 3$; $R^5$ and $R^6$ independently represent a hydrogen atom or an organic group having 1 to 30 carbon atoms; U represents any element belonging to the group of III, IV, or V in the periodic table, except for carbon and silicon; m2+m3+m4 is a number of valency determined by U; and each of m2, m3, and m4 is an integer of 0 or more.

* * * * *